(12) United States Patent
Bredno et al.

(10) Patent No.: US 8,660,333 B2
(45) Date of Patent: Feb. 25, 2014

(54) FUNCTIONAL IMAGING

(75) Inventors: Joerg Bredno, San Francisco, CA (US); Max Wintermark, Charlottesville, VA (US)

(73) Assignee: Koninklijke Philips N.V., Eindhoven (NL)

( * ) Notice: Subject to any disclaimer, the term of this patent is extended or adjusted under 35 U.S.C. 154(b) by 176 days.

(21) Appl. No.: 13/503,925

(22) PCT Filed: Oct. 14, 2010

(86) PCT No.: PCT/IB2010/054659
§ 371 (c)(1),
(2), (4) Date: Apr. 25, 2012

(87) PCT Pub. No.: WO2011/058459
PCT Pub. Date: May 19, 2011

(65) Prior Publication Data
US 2012/0288180 A1    Nov. 15, 2012

Related U.S. Application Data

(60) Provisional application No. 61/261,460, filed on Nov. 16, 2009.

(51) Int. Cl.
*G06K 9/00* (2006.01)
(52) U.S. Cl.
USPC .......................................................... 382/134
(58) Field of Classification Search
CPC ................................................ G01R 33/56366
See application file for complete search history.

(56) References Cited

U.S. PATENT DOCUMENTS

| | | | | |
|---|---|---|---|---|
| 8,032,202 | B2 * | 10/2011 | Omi et al. | 600/425 |
| 8,073,224 | B2 * | 12/2011 | Strobel et al. | 382/130 |
| 8,509,507 | B2 * | 8/2013 | Meetz et al. | 382/128 |
| 2004/0167395 | A1 | 8/2004 | Behrenbruch et al. | |
| 2008/0273782 | A1 * | 11/2008 | Ichihara | 382/131 |
| 2009/0028406 | A1 | 1/2009 | Arditi et al. | |
| 2009/0124898 | A1 * | 5/2009 | Stodilka et al. | 600/431 |
| 2009/0316970 | A1 * | 12/2009 | Kemper et al. | 382/131 |
| 2010/0204572 | A1 * | 8/2010 | Kalafut et al. | 600/431 |
| 2012/0033869 | A1 * | 2/2012 | Carlsen et al. | 382/131 |

FOREIGN PATENT DOCUMENTS

WO     2006086845  A1     8/2006

OTHER PUBLICATIONS

Brunecker, P., et al.; Correcting saturation effects of the arterial input function in dynamic susceptibility contrast enhanced MRI-a Monte Carlo simulation; 2007; Magnetic Resonance Imaging; 25(9)1300-1311.
Kim, S. M., et al.; Interindividual variability of arterial impulse response to intravenous injection of nonionic contrast agent (Iohexol) in DCE-CT study; 2009; Med. Phys.; 36(10)4791-4802.
Klotz, F, et al.; Perfusion measurements of the brain: using dynamic CT for the quantitative assessment of cerebral ischemia in acute stroke; 1999; European Journal of Radiology; 30(3)170-184.
Sa De Carmargo, E. C., et al.; Neuroimaging of Ischemia and Infarction; 2005; Journal of the American Society for Experimental NeuroTherapeutics, Inc.; 2(2)265-276.

* cited by examiner

*Primary Examiner* — Atiba O Fitzpatrick

(57) ABSTRACT

A method includes determining, via a processor, functional information about tissue of interest in image data for a functional image acquisition based on reference information generated based on non-tissue of interest.

20 Claims, 3 Drawing Sheets

FUNCTIONAL IMAGING

CROSS REFERENCE TO RELATED APPLICATIONS

This application claims the benefit of U.S. provisional application Ser. No. 61/261,460 filed Nov. 16, 2009, which is incorporated herein by reference.

The following generally relates to functional imaging and is described with particular application to computed tomography (CT). However, it also amenable to other imaging modalities such as magnetic resonance imaging (MRI), single photon emission computed tomography (SPECT), positron emission tomography (PET), ultrasound (US), and/or other imaging modalities that can acquire data used to determine functional information.

Various imaging modalities (e.g., CT, MRI, SPECT, PET, US, etc.) can be used for functional imaging. By way of example, a CT scanner can be used to perform a dynamic contrast-enhanced functional (or perfusion) CT imaging study that captures contrast agent uptake and washout in connection with tissue of interest. Such a study can be used to detect ischemia in the brain, differentiate between irreversibly damaged (infarcted) brain tissue and potentially reversibly damaged (at-risk) brain tissue based on the contrast agent dynamics in the brain tissue, stage tumors, determine the effectiveness of radiation treatment, etc.

With a typical functional CT brain study, a contrast agent bolus is administered (e.g., intravenously) to the patient, and a series of images of brain tissue of interest is successively acquired. The contrast agent causes the x-ray density of the brain to temporarily increase as the contrast agent flows through the vascular structure of the brain, and the images trace contrast agent flow through the vascular structure. As such, the resulting images show the perfusion dynamics of the contrast agent in the brain tissue of interest over time. This information can be used to determine quantitative information about the tissue of interest such as blood volume, blood perfusion, contrast agent permeation (leakage) rate through vessel walls, etc.

Generally, a quantitative analysis of functional information from image data requires reference information for the perfusion dynamics such as time-concentration curves, including a timing reference curve and a volume reference curve. A typical timing reference curve shows the dynamics of the contrast agent delivered to the tissue of interest and has been defined based on an arterial input function AIF(t), which provides contrast agent uptake information for the tissue of interest. A typical volume reference includes information used to quantify the amount of contrast agent that passes through the tissue of interest and has been determined from a venous outflow function VOF(t), which provides contrast agent washout information for the tissue of interest.

Such reference curves generally are only valid if they show the contrast agent concentration at an anatomically fixed point with no or minimal partial volume degradation. In other words, the reference curves should be determined based on a voxel in the image data that is substantially completely contained within reference tissue of interest (typically the lumen inside a blood vessel) in the image data. If the voxel moves out of the reference tissue of interest in the image data, then the uptake and/or washout of the contrast agent may not be suitably characterized and the contrast agent dynamics of the tissue of interest may not be well reflected in the reference curves.

Unfortunately, currently the only places in the image where it is possible to observe the concentration of a tracer in blood flowing through arteries are these arteries. An arterial diameter is usually small compared to the resolution of an image so that only very few voxels are actually located inside of the lumen of an artery. Depending on the imaging modality, the field of view, and the voxel size, all imaged arteries might be too small so that no voxel will "fit into an artery." As a consequence, many functional acquisitions exists were it is desired to determine a reference curve (the concentration of the tracer in the blood flowing into tissue of interest), but there is no position in the image where this curve can be observed.

Aspects of the present application address the above-referenced matters and others.

According to one aspect, a method includes determining, via a processor, functional information about tissue of interest in image data for a functional image acquisition based on reference information generated based on non-tissue of interest.

In another embodiment, an apparatus includes a functional analyzer having a processor that determines functional information about physiological tissue of interest in image data from a functional image acquisition based on reference information generated based on physiological tissue with normal functional characteristics.

In another embodiment, a computer readable storage medium includes instructions which, when executed by a computer, cause the computer to perform various acts such as determining functional information about physiological tissue of interest in image data for a functional image acquisition based on reference information generated based on non-tissue of interest.

The invention may take form in various components and arrangements of components, and in various steps and arrangements of steps. The drawings are only for purposes of illustrating the preferred embodiments and are not to be construed as limiting the invention.

Figure 1:
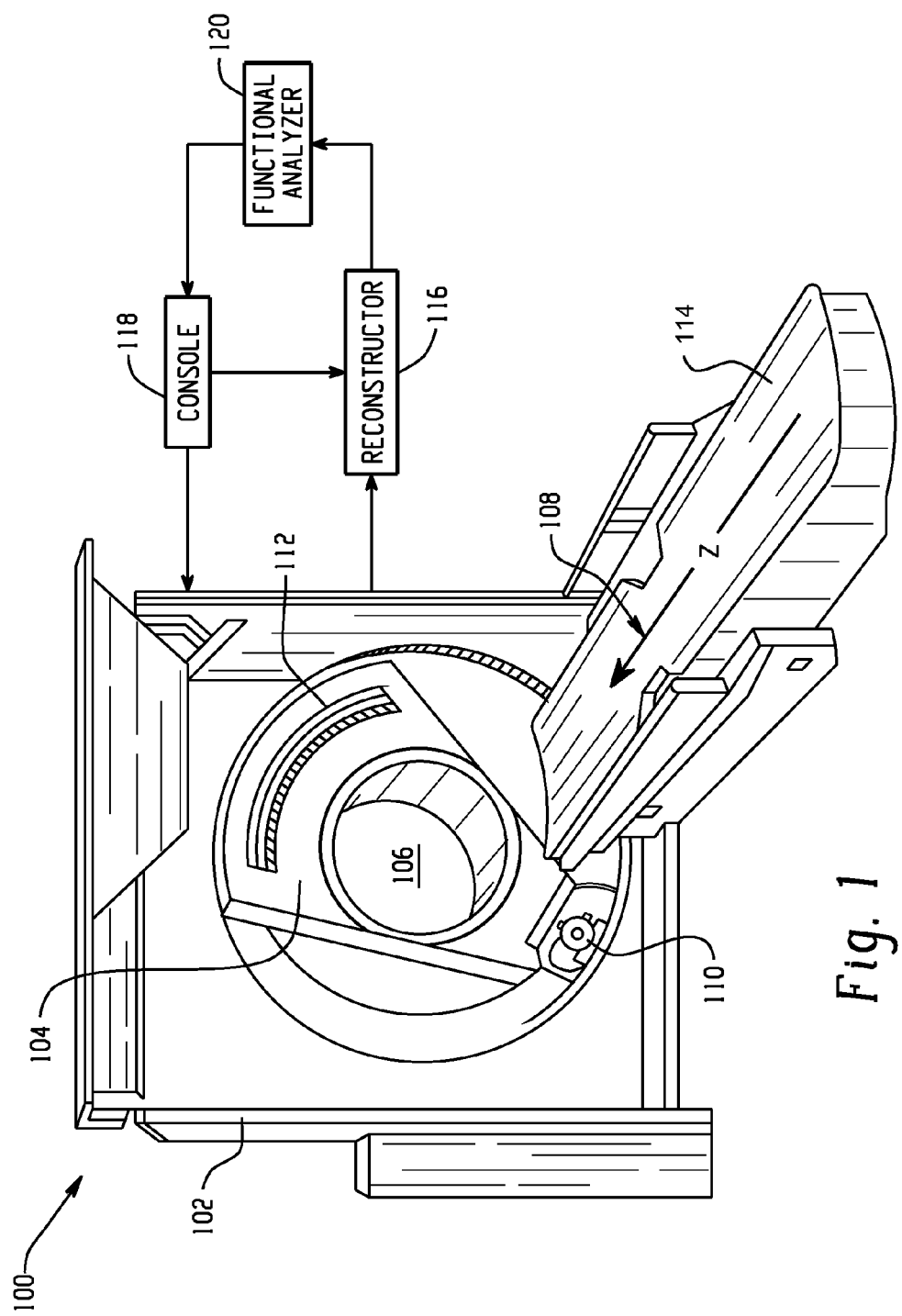
FIG. 1 illustrates an example imaging system in connection with a functional (image data) analyzer.

FIG. 1 illustrates an imaging system 100 such as a computed tomography (CT) scanner. The imaging system 100 includes a generally stationary gantry 102 and a rotating gantry 104. The rotating gantry 104 is rotatably supported by the stationary gantry 102 and rotates around an examination region 106 about a longitudinal or z-axis 108.

A radiation source 110, such as an x-ray tube, is supported by the rotating gantry 104. The radiation source 110 emits radiation from a focal spot and the radiation traverses the examination region 106 and an object or subject therein. A source collimator collimates the radiation to form a generally cone, wedge, fan or other shaped radiation beam.

A two-dimensional radiation sensitive detector array 112 subtends an angular arc opposite the radiation source 110 across the examination region 106. The detector array 112 includes a plurality of rows of detectors that extend along the z-axis direction. The detector array 112 detects radiation traversing the examination region 106 and generates projection data indicative thereof.

A patient support 114, such as a couch, supports an object or subject such as a human patient in the examination region 106.

A reconstructor 116 reconstructs the projection data and generates three-dimensional (3D) volumetric image data indicative thereof. The volumetric image data can be processed to generate one or more images of the object or subject.

A general-purpose computing system or computer serves as an operator console 118. A processor of the console 118 executes computer readable instructions encoded on computer readable storage medium of the console 118, which allows the operator to control operation of the system 100, including selecting scan protocols such as functional imaging protocols. The console 118 also includes input/output for receiving input and outputting information and a display for presenting information in a human readable format.

A functional (image data) analyzer 120 analyzes image data from functional based image acquisitions. An example of such an acquisition is a dynamic, contrast-enhanced study like a cerebral perfusion study performed to quantify blood flow in brain tissue. In such a study, a tracer or probe such as a bolus of a medium with one or more contrast agents is administered (e.g., intravenously, etc.) to the patient, and a series of images of the brain tissue of interest are successively acquired to capture contrast agent uptake and washout in the brain tissue. Another example study includes a liver study. Other acquisitions in which quantitative functional information can be derived from image data are also contemplated herein.

As described in greater detail below, in one instance the functional analyzer 120 functionally analyzes physiological tissue of interest based on one or more reference or time-concentration curves determined from known "normal" non-tissue of interest and expected functional values thereof. As such, reference curves can be obtained for the tissue of interest even though there may be no position in the image where these curves can be observed in the tissue of interest. As used herein, tissue of interest generally refers to diseased tissue of a particular type of tissue under study, and "normal" tissue (or non-tissue of interest) generally refers to non-diseased tissue of the same type of tissue as the tissue under study. By way of example, where the tissue of interest is brain tissue with perfusion characteristics believed to have been affected by a stroke, "normal" tissue or non-tissue of interest refers to brain tissue with perfusion characteristics believed to be unaffected by the stroke.

More particularly, with this approach, a region of tissue with known, normal functional values is first identified in the image data. The one or more time-concentration curves are then derived based on the dynamics of the tracer in the "normal" tissue from the image data. This can be achieved based on an iterative approach in which the parameters of an initial reference curve are tweaked until the reference curve produces an output corresponding to the expected output for the "normal" tissue. This reference curve can be displayed via the console 118 or other display device. Functional information for the tissue of interest can then be determined based on the time-concentration curves. Thus, functional information that conventionally has been determined from reference tissue of interest can now be reconstructed from time-concentration curves generated based on "normal" tissue.

The functional information can be used to generate blood flow (BF), blood volume (BV), mean transit time (MTT) and/or time to peak (TTP) maps, and/or other information such as leakage, permeability, standard uptake value (SUV), and/or other information. The above-noted maps and other information can be variously used, for example, for classifying tissue. By way of example, the maps and other information can be used to facilitate staging tumors, determining tumor aggressiveness, differentiating between infarction and at-risk tissue, planning radiation therapy, determining the efficacy of a planned radiation therapy, etc. From the foregoing, with this approach, perfusion related maps can be generated and analyzed without identification and/or correction of reference tissue of interest, and inaccuracies due to patient motion, partial volume degradation, etc. in reference tissue of interest can be mitigated.

The illustrated functional analyzer 120 can be part of a computing system that includes one or more processors that execute computer readable instructions encoded in computer readable storage medium thereof. In another embodiment, the functional analyzer 120 is part of or integrated with the console 118. In yet another embodiment, the functional analyzer 120 is separate from the system 100. In this instance, the functional analyzer 120 can be implemented as a single system or in a distributed manner across different systems. The system 100 and the functional analyzer 120 can communicate via wired or wireless communications technology.

Figure 2:
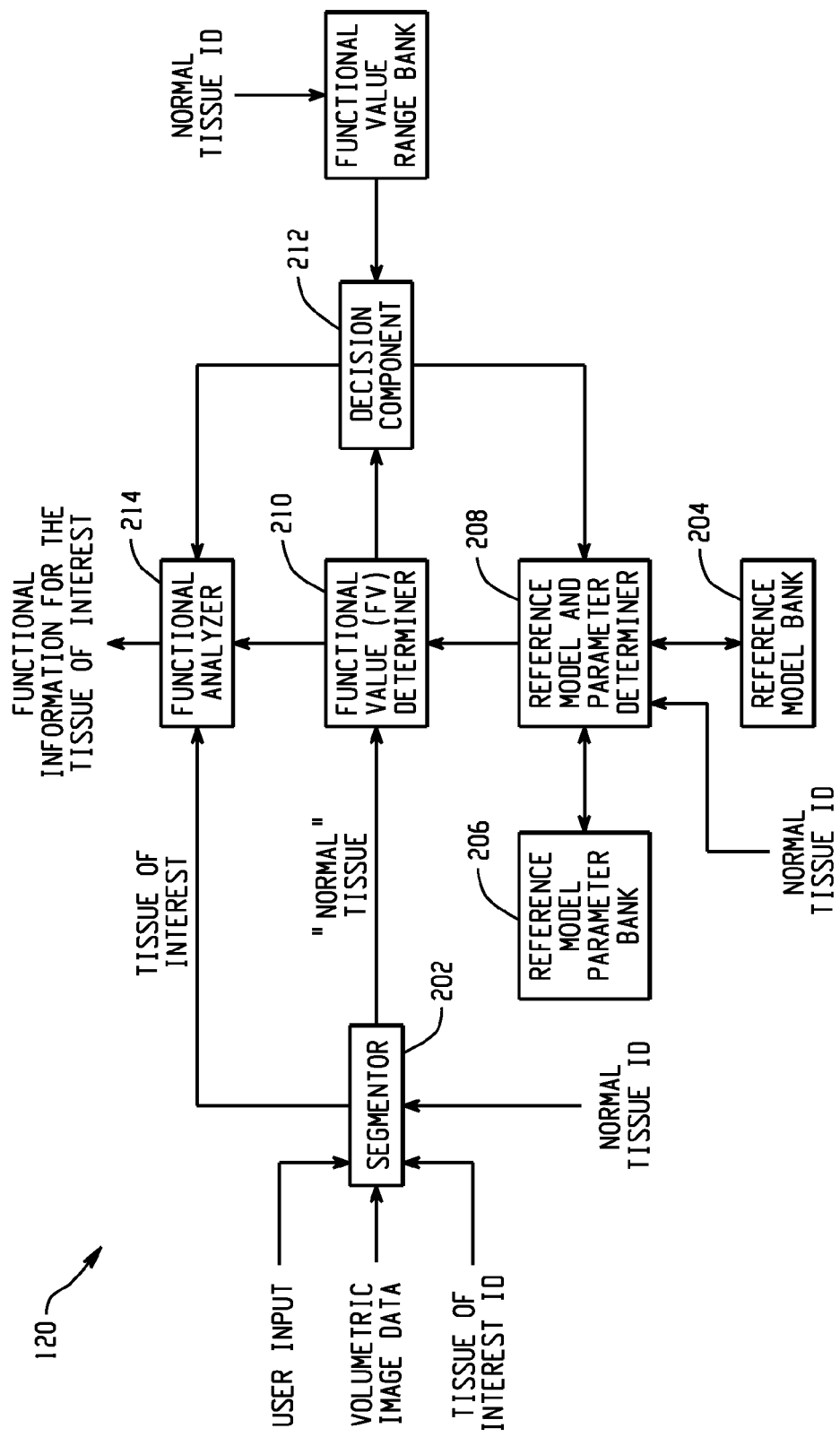
FIG. 2 illustrates an example of a functional (image data) analyzer.

FIG. 2 illustrates a non-limiting example of the functional analyzer 120 of FIG. 1.

A segmentor 202 segments image data. In one instance, the segmentor 202 automatically or manually (with user interaction and/or input) segments tissue of a patient represented in the image data automatically or manually identified as "normal" tissue, or tissue with functional values that are expected to be normal for the patient. As noted above, the "normal" tissue generally corresponds to the same type of tissue (e.g., liver) as the tissue of interest.

In the illustrated embodiment, the segmentor 202 segments the image data based on a normal tissue identifier (ID), which identifies the "normal" tissue. For example, in an acute ischemic stroke study, the non-affected brain hemisphere can be identified as "normal" tissue and used as reference input to quantify the perfusion deficit in the affected brain hemisphere. For a liver perfusion study, an automated or manual segmentation algorithm can identify and delineate the different liver segments and select one or more segments with "normal" perfusion as reference input used to quantify perfusion in the affected segments.

Additionally, the segmentor 202 automatically or manually segments tissue in the image data automatically or manually (e.g., with user input) identified as tissue of interest, which is the tissue being scanned and functionally analyzed. In the illustrated embodiment, the segmentor 202 segments the image data based on a tissue of interest identifier (ID), which identifies the tissue of interest. Continuing with the examples above, the segmentor 202 can automatically or manually identify and segment the non-affected brain hemisphere in the image data for quantitative analysis. For the liver perfusion study, the segmentor 202 can automatically or manually identify and delineate the different liver segments and select one or more segments for the functional analysis.

In the illustrated example, a reference model bank 204 stores pre-determined reference functional models. Such models can be tissue specific and created based on historical imaging studies and/or computer algorithms. Examples of such functional models include timing reference curve models, volume reference curve models, and/or models of other reference curves. A reference model parameter bank 206 stores one or more sets of pre-determined reference functional model parameters for the reference functional models. Likewise, the sets of parameters can be based on historical imaging studies and/or computer algorithms.

A reference model and parameter determiner 208 selects a reference functional model and corresponding parameters based on the "normal" tissue ID. In this example, the reference model and parameter determiner 208 initially selects a set of the pre-determined parameters stored in the reference model parameter bank 206 based on the "normal" tissue ID. In another embodiment, other information can be used as the initial parameters. For example, in another embodiment a default set of parameters, arbitrary values (e.g., all zeros), previously used values, optimized values, etc. can be used as the initial parameters.

A functional value (FV) determiner 210 determines functional values for the segmented "normal" tissue based on the selected reference functional model and the selected reference functional model parameters. Other information that may be taken into account when determining the functional values includes, but is not limited to, patient demographics, volume of the contrast agent bolus, patient history, etc. Examples of functional values include, but are not limited to, values indicative of one or more of blood flow, blood volume, permeability, leakage, etc. The FV determiner 210 outputs a signal indicative of the determined functional values.

A decision component 212 compares the output signal with pre-determined ranges for the functional values for the "normal" tissue. For example, if the "normal" tissue is brain tissue, then the pre-determined ranges of functional values correspond to ranges of expected functional values for "normal" brain tissue.

If a functional value falls outside of a functional value range, the decision component 212 notifies the reference model and parameter determiner 208, which modifies the input model parameters for the selected reference functional model, and the FV determiner 210 computes and outputs a signal indicative of the newly determined functional values. The above process can continue until the determined functional values fall within the functional value ranges, a pre-determined percentage of the functional value ranges, a pre-determined time period lapses, a pre-determined number of iterations are performed, and/or some other gating criteria is satisfied.

Once a set of functional values are within the functional value ranges, the decision component 212 outputs a signal that indicates that the set of functional values are within the functional value range.

A functional analyzer 214, in response to the signal from the decision component 212, determines functional information for the segmented tissue of interest based on the reference functional model and the reference functional model parameters that resulted in functional values that satisfied the functional value ranges for the segmented "normal" tissue.

In the above example, pre-determined reference models from the bank 204 are used. In another embodiment, reference curves are created from segmented tissue of interest in the image data. This includes using portions of the tissue of interest in the image data that are not suitable for quantitative analysis of the perfusion of the tissue of interest, for example, portions that do not continually cover a voxel throughout the series of image data. Using such portions may provide for initial reference curves that are more indicative of the true perfusion dynamics of the tissue of interest relative to the pre-determined reference curves.

Figure 3:
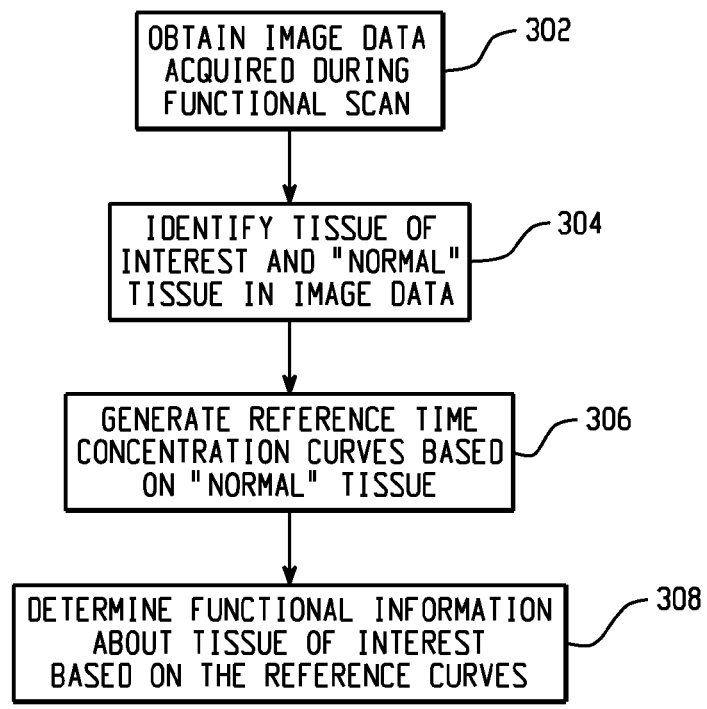
FIG. 3 illustrates a method for determining functional information for tissue of interest based on reference information generated based on non-tissue of interest.

FIG. 3 illustrates a method for determining functional information for tissue of interest based on reference information derived from non-tissue of interest.

At 302, image data from a functional image acquisition capturing tissue of interest is obtained. As noted herein, such a study may include administering a tracer and continually imaging the patient to follow the tracer through the tissue of interest. The image data may be generated from the imaging system 100 of FIG. 1 or another imaging system. In addition, the image data can be obtained from the imaging system and/or storage storing the image data.

At 304, the image data is segmented to identify or locate tissue of interest and tissue having "normal" perfusion characteristics. By way of example, where the tissue of interest is a first portion of the brain possibly affected by a stroke, the "normal" tissue may be a different portion of the brain not affected by the stroke. As noted herein, automatic and/or manual segmentation techniques can be used.

Figure 4:
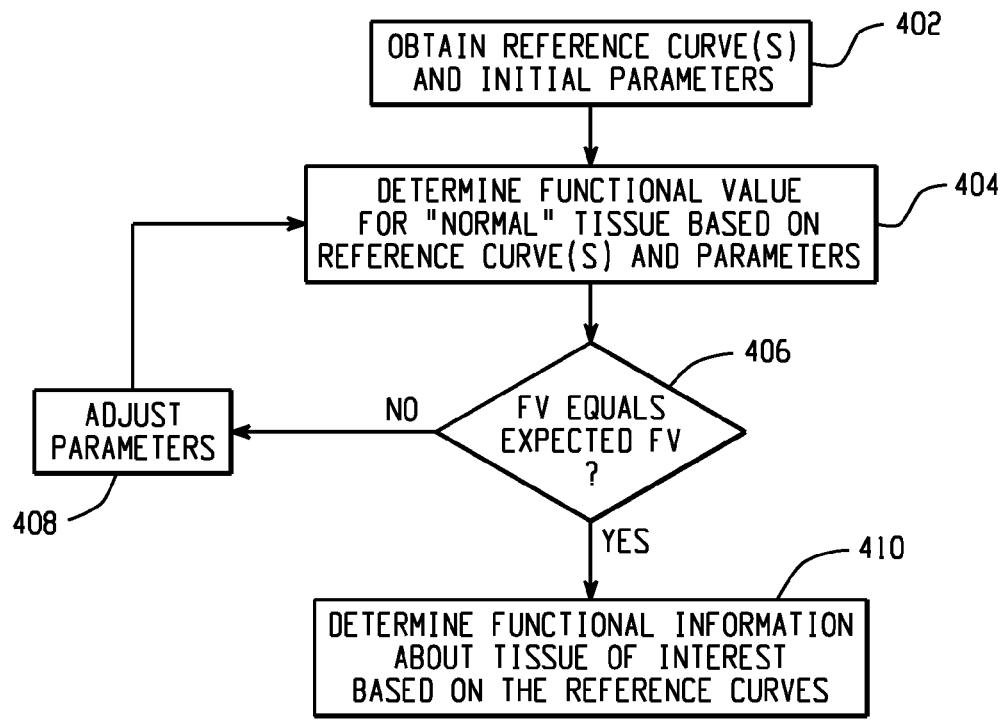
FIG. 4 illustrates a method for determining the reference information based on the non-tissue of interest.

At 306, one or more reference time-concentration curves are generated based on the segmented "normal" tissue and expected dynamics of the contrast in the "normal" tissue. FIG. 4, which is discussed below, describes one non-limiting approach to generating such reference time-concentration curves.

At 308, functional information for the segmented tissue of interest is determined based on the one or more reference time-concentration curves generated based on the segmented "normal" tissue. The functional information may be used to generate perfusion maps such as BF, BV, MTT, TTP maps, determine information such as leakage, permeability, SUV, etc., and/or generate other functional information for the tissue of interest.

FIG. 4 illustrates a method for generating reference time-concentration curves.

At 402, a reference curve(s), such as a pre-determined general curve or a curve generated based on reference tissue not suitable for quantitative analysis is obtained.

At 404, functional values for the "normal" tissue (which is identified at act 304 of FIG. 3) are generated based on the reference curve(s) and input parameters.

At 406, it is determined whether the generated functional values fall within a range of expected functional values for the "normal" tissue.

If not, then at 408 the input parameters of the reference curve are adjusted, and acts 404 to 406 are repeated.

If so, then at 410 the model reference curve and parameters are used to determine the functional information for the tissue of interest as described herein, for example, in connection with act 308 of FIG. 3.

The acts described herein may be implemented by way of computer readable instructions, which, when executed by a computer processor(s), causes the processor(s) to carry out the acts described herein. In such a case, the instructions are stored in a computer readable storage medium such as memory associated with and/or otherwise accessible to the relevant computer.

It is to be appreciated that the foregoing can be applied to essentially all functional imaging applications and analyses that use reference input curves. Such applications include CT, MRI, SPECT, PET, US, and/or other imaging applications.

The invention has been described herein with reference to the various embodiments. Modifications and alterations may occur to others upon reading the description herein. It is intended that the invention be construed as including all such modifications and alterations insofar as they come within the scope of the appended claims or the equivalents thereof.

What is claimed is:

1. A method, comprising:

determining, via a processor, functional information about tissue of interest in image data for a functional image acquisition based on reference information generated based on non-tissue of interest, wherein the functional information about the tissue of interest includes a time-concentration curve and the reference information includes one or more time-concentration curves representing tracer dynamics in the non-tissue of interest.

2. The method of claim 1 further including displaying the reference information.

3. The method of claim 1, wherein the tissue of interest and the non-tissue of interest are a same type of physiological tissue.

4. The method of claim 1, further comprising:
computing functional values for the non-tissue of interest based on a model reference curve and initial model reference curve parameters; and
employing the model reference curve and the initial model reference curve parameters as the reference information in response to the computed functional values satisfying pre-determined criteria.

5. The method of claim 4, wherein the pre-determined criteria includes a range of expected functional values for the non-tissue of interest.

6. The method of claim 4, wherein the model reference curve is generated based on a portion of the tissue of interest in the image data not suited for determining the functional information.

7. The method of claim 4, further comprising:
adjusting the initial model reference curve parameters in response to the computed functional values falling outside of the pre-determined criteria.

8. The method of claim 7, wherein the model reference curve parameters are iteratively adjusted until the computed functional values satisfy exit criteria.

9. The method of claim 7, further comprising:
employing the model reference curve and the adjusted model reference curve parameters as the reference information.

10. The method of claim 1, further comprising:
generating at least one of a blood flow map, a blood volume map, a mean transit time map, or time to peak map based on the functional information.

11. An apparatus, comprising:
a functional analyzer having a processor that determines functional information about physiological tissue of interest in image data from a functional image acquisition based on reference information generated based on non-tissue of interest physiological tissue with normal functional characteristics, wherein the functional information about tissue of the interest includes a time-concentration curve and the reference information includes one or more time-concentration curves representing tracer dynamics in the non-tissue of interest.

12. The apparatus of claim 11, further including displaying the reference information.

13. The apparatus of claim 11, further comprising:
a functional value determiner that computes functional values for the normal tissue based on a model reference curve and initial model reference curve parameters.

14. The apparatus of claim 13, wherein the functional analyzer employs the model reference curve and the initial model reference curve parameters as the reference information in response to the computed functional values satisfying pre-determined criteria.

15. The apparatus of claim 13, further comprising:
a reference model and parameter determiner that determines the model reference curve and the initial model reference curve parameters based on a type of the normal tissue.

16. The apparatus of claim 15, wherein the reference model and parameter determiner modifies the initial model reference curve parameters in response to the computed functional values falling outside of the pre-determined criteria.

17. The apparatus of claim 16, wherein the pre-determined criteria includes a range of expected functional values for the normal tissue.

18. The apparatus of claim 16, wherein the model reference curve parameters are iteratively modified until the computed functional values satisfy the pre-determined criteria.

19. The apparatus of claim 13, further comprising:
a decision component that determines whether the functional values for the normal tissue satisfy the expected functional values for the normal tissue.

20. A non-transitory computer readable storage medium containing instructions which, when executed by a computer, cause the computer to perform the act of:
determining functional information about physiological tissue of interest in image data for a functional image acquisition based on reference information generated based on non-tissue of interest, wherein the functional information about the tissue of interest includes a time-concentration curve and the reference information includes one or more time-concentration curves representing tracer dynamics in the non-tissue of interest.

* * * * *